US00PP14779P2

(12) United States Plant Patent
Bessho

(10) Patent No.: US PP14,779 P2
(45) Date of Patent: May 11, 2004

(54) CALIBRACHOA PLANT NAMED 'KAKEGAWA S46'

(50) Latin Name: *Calibrachoa sp.*
Varietal Denomination: Kakegawa S46

(75) Inventor: Masao Bessho, Kakegawa (JP)

(73) Assignee: Sakata Seed Corporation (JP)

( * ) Notice: Subject to any disclaimer, the term of this patent is extended or adjusted under 35 U.S.C. 154(b) by 0 days.

(21) Appl. No.: 10/401,813

(22) Filed: Mar. 28, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Jondle & Associates PC

(57) ABSTRACT

'Kakegawa S46' is a new variety of Calibrachoa plant. This new variety has light yellow flowers and dark green foliage.

1 Drawing Sheet

Botanical classification: *Calibrachoa sp.*
Variety denomination: 'Kakegawa S46'.

BACKGROUND OF THE INVENTION

'Kakegawa S46' originated from a hybridization made in November 1998 in Kakegawa, Japan. The female parent was a Calibrachoa breeding line with violet colored flowers known as 7BC-38A. The male parent was Calibrachoa variety 'Kakegawa S27', U.S. Plant Pat. No. 13,044P2.

In February 1999, $F_1$ seed was sown from this cross and 30 plants were transplanted to outdoors. Various shades of rose and yellow flowered plants were observed. Three plants with light yellow flowers were selected. In August 1999 these plant lines were then vegetatively propagated and grown to flowering stage in pots. Trait stability was evaluated during the summer of 2000 in greenhouses in Japan.

The breeder selected one line, for its flower color and abundance, to be vegetatively propagated and further evaluated in Salinas, Calif. during 2001. This selection was subsequently named 'Kakegawa S46' and was determined to have its trait characteristics firmly fixed.

DESCRIPTION OF PHOTOGRAPH

This new Calibrachoa plant is illustrated by the accompanying photographs which show blooms, and foliage of the plant in full color, the colors shown being as true as can be reasonably obtained by conventional photographic procedures.

DESCRIPTION OF THE GENUS CALIBRACHOA LLAVE & LEX

Figure 1:
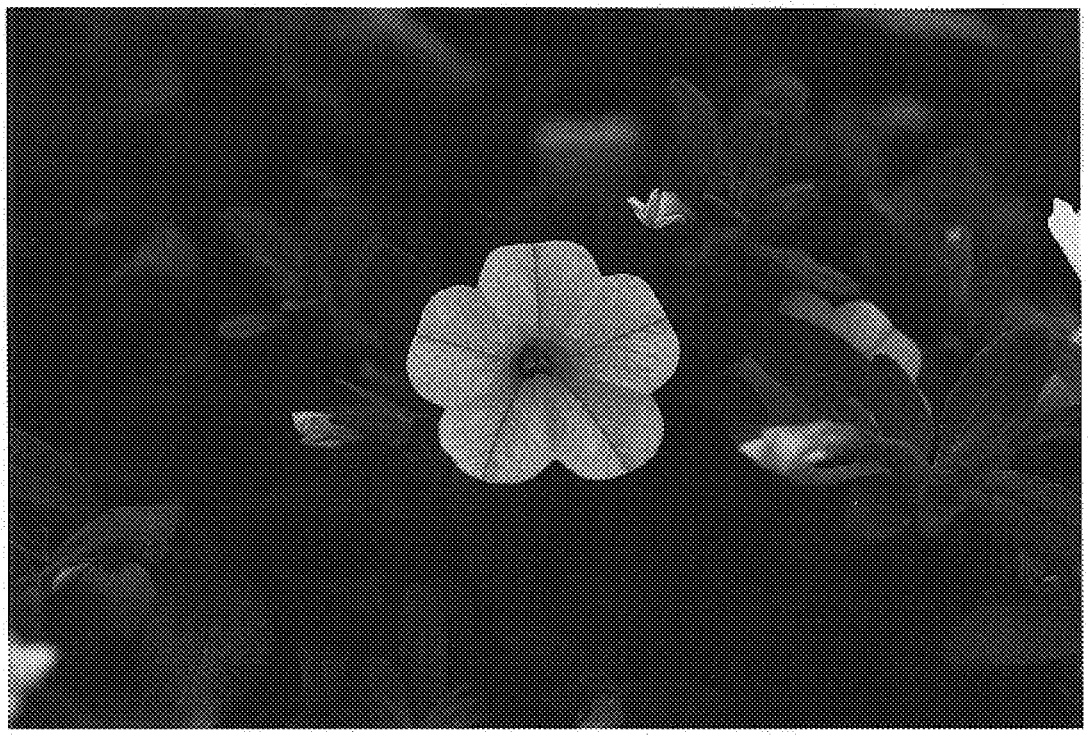
FIG. 1 shows the mature inflorescence.
Figure 2:
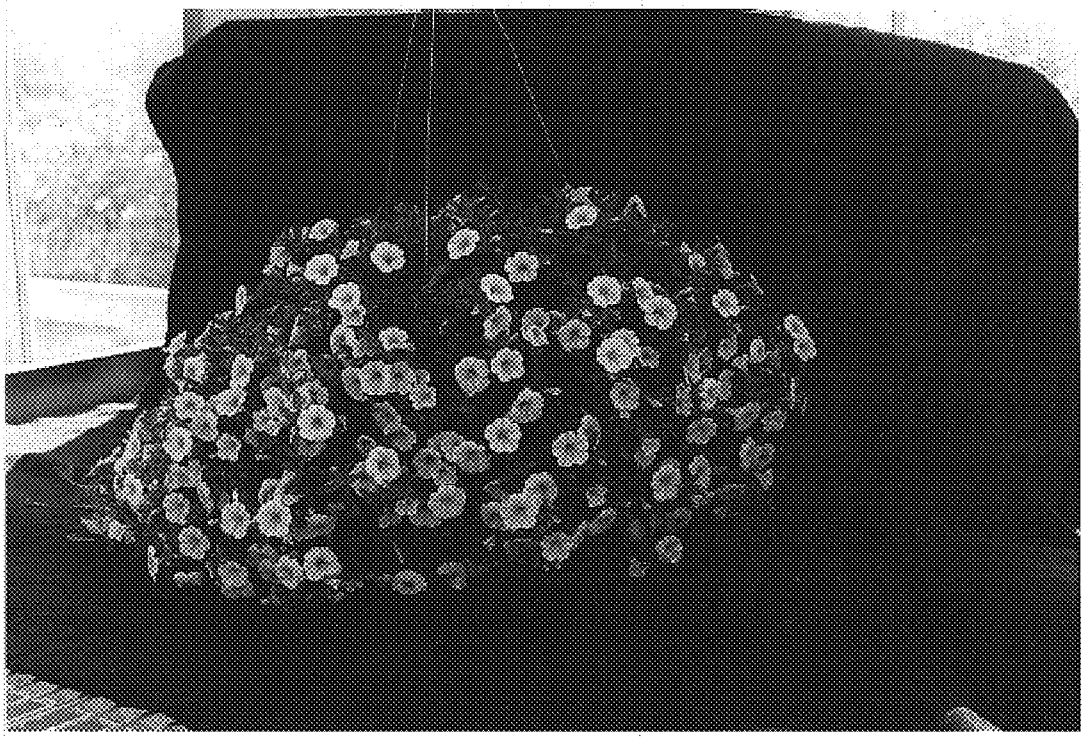
FIG. 2 shows the entire plant.

The genus Petunia was originally established in 1803 by A. L. Jussieu, who described both *P. parviflora* and *P. nyctaginifloa* as type species. Using a non-horticultural system that selected the first mentioned species as the type species (lectotype), N. L. Britton and H. A. Brown declared *P. parviflora* as the type species for Petunia in 1913.

During the 1980's and 1990, H. J. Wijsman published a series of articles regarding the ancestry of P. hybrida, the Garden Petunia, and the inter-relationship of serveral species classified as Petunia. These studies discovered that P. hybrida and its ancestrial species, *P. nyctaginiflora* (=*P. axillaris*) and *P. violacea* (=*P. integrifolia*), possessed 14 pairs of chromosomes while several other species, including *P. parviflora*, possessed 18 pairs of chromosomes. Since *P. parviflora* was the lectotype species for the Petunia genus, Wijsman and J. H. de Jong proposed transferring the 14 chromosome species to the genus Stimoryne. Horticulturists opposed reclassifying the Garden Petunia and in 1986, Wijsman proposed the alternative of making *P. nyctaginiflora* the lectotype species for Petunia and transferring the 18 chromosome species to another genus. The I. N. G. Committee adopted this proposal. By 1990 Wijsman had transferred several species, including *P. parviflora* (=*C. parviflora*) to Calibrachoa, originally established by Llave and Lexarza in 1825. *Calibrachoa paraviflora* (=*C. mexicana* Llave & Lexarza) is now the type species for the genus Calibrachoa.

Classification of the current Petunia and Calibrachoa species is still in progress. New species are also being identified. Consequently a proper description has not been written for the Calibrachoa genus. Calibrachoa can, however, be distinguished from Petunia based on the higher chromosome number, chromosome morphology, plant branching habit and type of flower bud aestivation. Whereas Petunia species bear a flower peduncle and one new stem from a node, Calibrachoa bear a flower peduncle and three stems. Petunia species have a chochlear corolla bud, a single outermost petal covers the other four, radially folded and terminally contorted petals. Calibrachoa flower buds are flat with all five petals linearly folded and the two lower petals forming a cover around the three other petals and fused together.

ENVIRONMENTAL CONDITIONS FOR PLANT GROWTH

The terminal 1.0 to 1.5 inches of an actively growing stem was excised. The base of the cuttings were dipped for 1 to 2 seconds in a 1:9 solution of Dip 'N Grow (1 Dip 'N Grow: 9 water) root inducing solution immediately prior to sticking into the cells trays. Cutting were stuck into plastic cell trays having 98 cells, and containing a moistened peat moss-based growing medium. The cuttings were misted with water from overhead for 10 seconds every 30 minutes until sufficient roots were formed. The vegetative cuttings were propagated in five to six weeks.

Rooted cuttings were transplanted and grown in 20 cm diameter plastic pots in a glass greenhouse. Pots contained a peat moss-based growing medium. Soluble fertilizer containing 20% nitrogen, 10% phosphorus and 20% potassium was applied once a day or every other day. Fertilizer was applied in irrigation water. Pots were top-dressed with a slow release fertilizer containing 20% nitrogen, 10% phosphorus and 18% potassium. The typical average air temperature was 24C.

DETAILED DESCRIPTION OF THE NEW PLANT

The following traits and characteristics describe the new variety.

Classification:
- *Family.*—Solanaceae.
- *Species.*—Calibrachoa spp.
- *Common names.*—Petunia.

Parentage:
- *Female parent.*—Breeding line 7BC–38A. (Not patented).
- *Male parent.*—*'Kakegawa S27'*, U.S. Plant Pat. No. 13,044P2.

Growth:
- *Habit.*—Decumbent, mounding in center.
- *Height.*—23.0 cm.
- *Spread.*—115.0 cm when grown in a 41 cm hanging basket or pot, and using five 20 cm potted plants in one hanging basket.
- *Life cycle.*—Tender perennial.
- *Time to produce a rooted cutting.*—6 weeks.
- *Time to bloom from propagation.*—10 weeks.
- *Flowering season.*—Spring and summer.
- *Flowering requirements.*—No particular requirements, day neutral.
- *Resistance/susceptibility.*—Excellent resistance to rain, heat and drought. Will not tolerate temperatures below 10C. Plants are susceptible to Botrytis, powdery mildew, various stem and root rots, and certain viruses, like Tobacco Mosaic Virus and Impatiens Necrotic Spotted Virus. Plants can be infested with aphids, leafminer, whitefly and various Lepitopdera.
- *Form.*—Branching, dense.

Stems:
- *Stem color.*—R.H.S. 144B (yellow-green).
- *Anthocyanin color.*—None.
- *Pubescence.*—Heavy.
- *Pubescence color.*—Clear.
- *Pubescence shape.*—Pointed.
- *Stem description.*—Round, slightly, ancipital.
- *Stem diameter.*—2.0 mm.
- *Internode.*—1.5 to 2.5 cm.

Leaves:
- *Leaf tip* .—Mucronate.
- *Leaf arrangement.*—Alternate.
- *Leaf base.*—Decurrent.
- *Leaf color.*—Upper surface: R.H.S. 137A (green); lower surface: R.H.S. 138A (green).
- *Leaf fragrance.*—Absent.
- *Leaf margin.*—Entire.
- *Leaf surface.*—Rough.
- *Leaf surface pubescence.*—Slight.
- *Leaf surface pubescence.*—Clear.
- *Leaf variegation.*—No.
- *Leaf length.*—4.0 cm.
- *Leaf shape.*—Elliptical.
- *Leaf width.*—8.0 mm–10 mm.

Flowers:
- *Calyx.*—5 sepals; 3.0×2.0 cm (l×w); free.
- *Corolla.*—5 petals, fused.
- *Flower diameter.*—1.5 cm.
- *Bud color.*—R.H.S. N144C (yellow-green).
- *Bud shape.*—Ovate.
- *Bud surface.*—Pubescent.
- *Ovary.*—Superior.
- *Duration of flower life.*—5 days.
- *Flowering habit.*—Indeterminate.
- *Placenta arrangement.*—Central.
- *Inflorescence type.*—Solitary.
- *Stamens.*—Free.
- *Stamen color.*—R.H.S. 1D (yellow-green).
- *Stigma color.*—R.H.S. 142A (green).
- *Style color.*—R.H.S. 142C (green).
- *Petal size.*—2.0 cm×1.0 cm (1×w).
- *Petal color.*—Upper surface: R.H.S. 4D (yellow) with R.H.S. 14C (yellow-orange) corolla throat and mid-veins; lower surface: R.H.S. 8A (yellow) with RHS 14C (yellow-orange) corolla mid-veins; corolla tube: inner surface: R.H.S. 8A (yellow); outer surface R.H.S. 8B (yellow); RHS 14C (yellow-orange) veins.
- *Petal pubescence.*—Glabrous.
- *Pollen color.*—R.H.S. 3C (yellow).
- *Produces seed.*—None.

COMPARISON WITH MOST SIMILAR VARIETY

'Kakegawa S46' is a distinct variety of Calibrachoa owing to its light yellow flower with yellow-orange corolla throat and petal mid veins. 'Kakegawa S46' is most similar to the variety 'Million Bells Trailing Yellow' however there are numerous differences as shown in the table below.

| Characteristics | 'Kakegawa' | 'Million Bells Trailing Yellow' |
|---|---|---|
| Leaf Length | 3 cm | 5 cm |
| Flower Diameter | 1.5 cm | 2.8 cm |
| Petal Color | Light Yellow, RHS 4D | Dark yellow-orange, RHS 12A |

What is claimed is:

1. A new and distinct Calibrachoa plant as shown and described herein.

* * * * *